(12) United States Patent
Slanina et al.

(10) Patent No.: US 7,405,298 B2
(45) Date of Patent: Jul. 29, 2008

(54) PROCESS FOR MAKING RISPERIDONE AND INTERMEDIATES THEREFOR

(75) Inventors: Pavel Slanina, Lelekovice (CZ); Jiri Bartl, Strelice (CZ)

(73) Assignee: Synthon IP Inc., Gainesville, VA (US)

( * ) Notice: Subject to any disclaimer, the term of this patent is extended or adjusted under 35 U.S.C. 154(b) by 435 days.

(21) Appl. No.: 10/705,926

(22) Filed: Nov. 13, 2003

(65) Prior Publication Data

US 2004/0097523 A1      May 20, 2004

Related U.S. Application Data

(60) Provisional application No. 60/425,727, filed on Nov. 13, 2002.

(51) Int. Cl.
*C07D 487/04*      (2006.01)
*C07D 211/12*      (2006.01)

(52) U.S. Cl. .................................. 544/282; 546/229

(58) Field of Classification Search ................. 544/282; 546/192, 229
See application file for complete search history.

(56) References Cited

U.S. PATENT DOCUMENTS

| 3,946,022 | A | * | 3/1976 | Carr et al. ................. 546/191 |
| 4,335,127 | A | | 6/1982 | Vandenberk et al. |
| 4,342,870 | A | | 8/1982 | Kennis et al. |
| 4,408,054 | A | * | 10/1983 | Strupczewski et al. ...... 546/226 |
| 4,804,663 | A | * | 2/1989 | Kennis et al. .......... 514/259.41 |

FOREIGN PATENT DOCUMENTS

| EP | 0 453 042 B1 | 10/1991 |
| EP | 0 196 132 B1 | 8/1992 |
| EP | 0 368 388 B1 | 5/1995 |
| ES | 2 050 069 | 5/1994 |
| ES | 2050069 | * 5/1994 |
| ES | 2 074 966 | 9/1995 |
| WO | WO 01/85731 A1 | 11/2001 |
| WO | WO 02/12200 A1 | 2/2002 |
| WO | WO 02/14286 A1 | 2/2002 |
| WO | WO 03/042212 A1 | 5/2003 |
| WO | WO 2005066165 | * 7/2005 |

* cited by examiner

*Primary Examiner*—Brenda Coleman
*Assistant Examiner*—Susanna Moore
(74) *Attorney, Agent, or Firm*—Mark R. Buscher

(57) ABSTRACT

The formation of risperidone is enhanced by the use of enriched Z-isomer oxime intermediate(s) of formula (3) or (7).

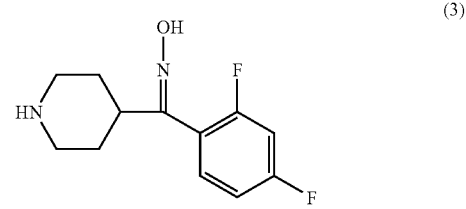

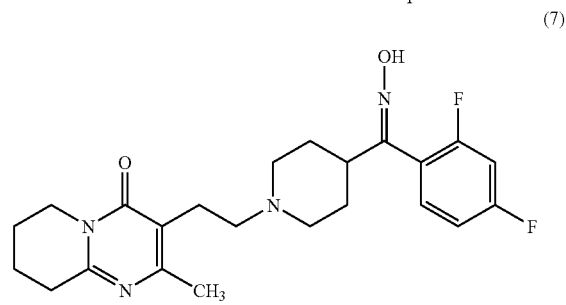

The oxime(s) can be isomerically enriched by a variety of techniques including the use of the novel acetic acid salt thereof, which affords, inter alia, resolution of the isomers and/or by heat conversion.

10 Claims, No Drawings

PROCESS FOR MAKING RISPERIDONE AND INTERMEDIATES THEREFOR

This application claims the benefit of priority under 35 U.S.C. § 119(e) from U.S. provisional patent application Ser. No. 60/425,727, filed Nov. 13, 2002, the entire contents of which are incorporated herein by reference.

BACKGROUND OF THE INVENTION

Risperidone, or 3-[2-[4-(6-Fluoro-1,2-benzisoxazol-3-yl)-1-piperidinyl]-ethyl]-6,7,8,9-tetrahydro-2-methyl -4-H-pyrido[1,2-a]-pyrimidin-4-one, is a serotonin antagonist approved for the treatment of psychotic disorders such as schizophrenia. Its structure is shown in formula (1).

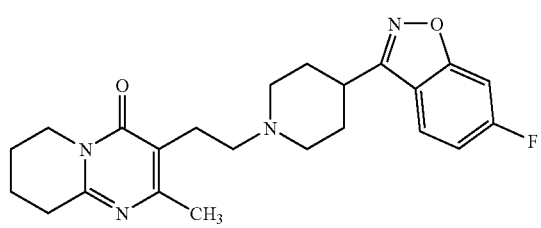
(1)

The compound and its pharmaceutical activity are identified in U.S. Pat. No. 4,804,663.

Various methods for making risperidone are known. Typically the synthesis includes forming the benzisoxazole ring moiety by cyclizing an oxime intermediate. For example, U.S. Pat. No. 4,804,663, which corresponds to EP 196132, discloses oximating a 4-(2,4-difluorobenzoyl)piperidine hydrochloride (2)

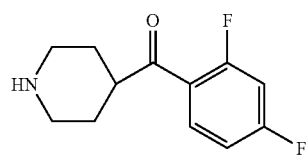
(2)

by treating with hydroxylamine to yield a corresponding oxime (3).

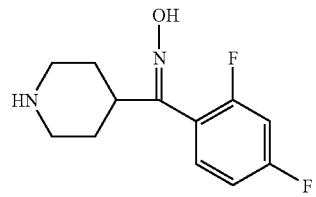
(3)

The oxime is cyclized by a base in water to yield 6-fluoro-3-(4-piperidinyl)-1,2-benzizoxazole, compound (4) in approximately 62% yield.

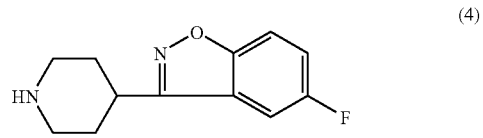
(4)

The benzisoxazole compound (4) is N-alkylated with the 3-(2-chloroethyl)-2-methyl-6,7,8,9-tetrahydro-4H-pyrido[1,2a]pyrimidin-4-one hydrochloride, compound (5)

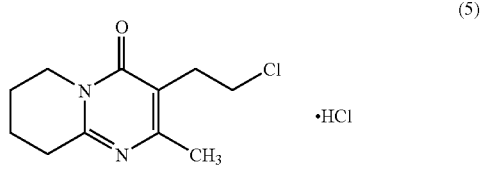
(5)

in the presence of sodium carbonate and potassium iodide in dimethylformamide, to yield risperidone base in a relatively low yield (46%). This last step was reportedly improved in WO 02/14286 and in WO 02/12200 by replacing the dimethylformamide with acetonitrile, isopropanol, methyl ethylketone or iso-butanol as the solvent.

An alternative oxime route is described in ES 2050069 wherein the starting piperidine compound (2) is first N-alkylated with the pyridopyrimidinone compound (5), under essentially the same alkylation conditions as above, to yield (63%) of a dihydrochloride of an alkylated ketone compound (6).

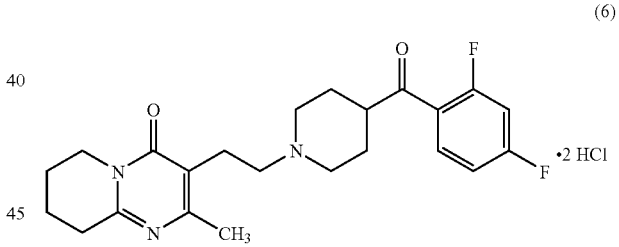
(6)

The ketone (6) is oximated by hydroxylamine hydrochloride to yield (76%) of an alkylated oxime (7).

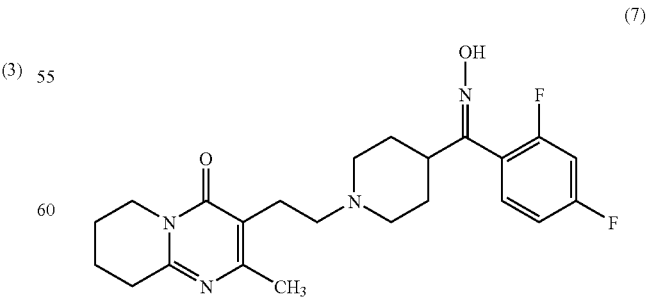
(7)

The oxime (7) is then cyclized in the presence of a base in 80-85% yield to the desired risperidone base.

In addition to these prior art procedures, another oxime-based synthesis route has been proposed for compounds analogous to risperidone in EP 368 888 and in EP 453042. While not applied to risperidone, the general scheme suggests forming an oxime analogous to the compound of (7) by first converting a ketone (2) to the oxime (3). This oxime is then alkylated, prior to cyclization, by the corresponding pyridopyrimidine compound to yield an alkylated oxime analogous to compound (7). As in ES 2050069, the last step is to cyclize the oxime to form the benzisoxazole ring.

The use of a different oxime compound in forming risperidone is suggested in Spanish Patent No. 2,074,966. In this patent a pyran-containing oxime of the formula

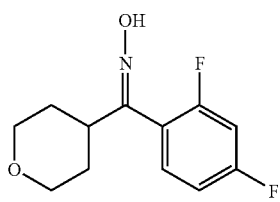

is formed. After cyclization to form the isoxazole ring, the pyran ring is opened and ultimately reacted with an aminopyridopyrimidinone compound to form risperidone. The patent also discloses the isolation of the "syn" isomer of the oxime molecule, using chromatographic methods, from the crude mixture having a "syn/anti" ratio of 3:1.

It would be desirable to provide another useful method and reagents for making risperidone, especially a method and reagents that can provide for improved results.

SUMMARY OF THE INVENTION

The present invention relates to a process for making risperidone and certain intermediates useful therein. In particular, one aspect of the present invention relates to an acetic acid salt compound of formula (3) or (7):

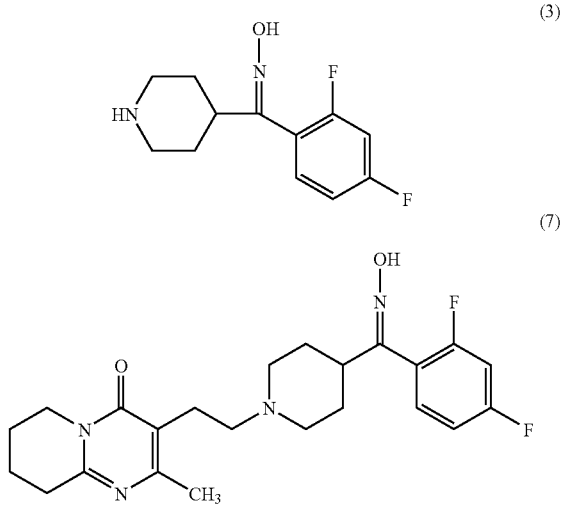

Preferably, the acetic acid salt is in solid form and is at least 90% isomerically pure Z-isomer of formula (3) or (7).

Another aspect of the present invention relates to a process, which comprises reacting acetic acid with a compound of formula (3) or (7) to form the acetic acid salt thereof. Preferably, the acetic acid salt is isolated in solid form and contains more of a Z-isomer than an E-isomer.

A further aspect of the invention relates to an enriched Z-isomer oxime of formula (3) or (7) or a salt thereof, wherein the amount of Z-isomer is at least 80%, preferably at least 90%, and more preferably at least 95% based on the total amount of the oxime.

A still further aspect of the invention relates to a process, which comprises providing an enriched Z-isomer of a compound of formula (3) or (7) or salt thereof, wherein said oxime contains 80% of said Z-isomer; and converting said Z-isomer into risperidone. In one embodiment the enriched Z-isomer oxime can be provided by preferentially precipitating the Z-isomer as an acetic acid salt from a solution containing the oxime in Z- and E-isomer forms and isolating the precipitated Z-isomer oxime. Alternatively, the enriched Z-isomer oxime can be provided by heating an oxime of formula (3) or (7), which contains the E-isomer, in a solvent, to convert sufficient E-isomer into Z-isomer. Preferably, the conversion is performed in the presence of an acid or a salt of an acid.

Accordingly, another aspect of the invention relates to a method which comprises reacting in a solvent and in the presence of acetic acid, a compound of formula (2),

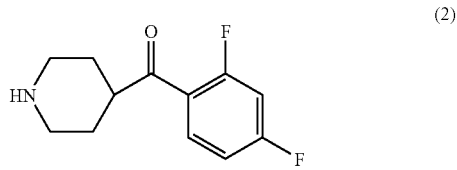

with a hydroxylamine to form Z- and E-oxime isomers of formula (3) wherein substantially upon formation said Z-isomer precipitates as an acetic acid salt thereof.

Finally, the invention relates to a process, which comprises preferentially precipitating an acetic acid salt of a Z-isomer of formula (3) or (7) from a solution containing a mixture of Z- and E-isomers thereof.

DETAILED DESCRIPTION

It has been discovered that although oximes (3) and (7) are formed as a mixture of Z and E geometric isomers in the prior synthetic schemes, essentially only the Z-isomer cyclizes to a benzisoxazole ring in risperidone synthesis. Thus, the method of producing risperidone can be enhanced by providing an enriched Z isomer oxime. Further, this surprisingly led to the discovery that the Z and E isomer oxime can be readily separated from one another when converted into an acetic acid salt form. Accordingly, an acetic acid salt is a convenient way to provide an enriched isomer oxime. Based on these and further discoveries the present invention has been made.

Accordingly, the present invention relates to a process of making risperidone using enriched oxime isomers. The process includes providing an enriched Z-isomer oxime of a compound of formula (3) or (7) or a salt thereof and converting it into risperidone. An "enriched Z-isomer oxime" means that the oxime contains at least 80% of the Z-isomer form of the oxime compound. The Z- and E-isomer oximes can generally be represented as follows with reference to formula (3):

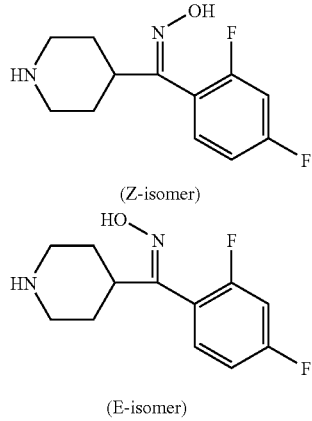

(Z-isomer)

(E-isomer)

In the Z-isomer, the terminal hydroxyl group is near to the fluorine atom on the phenyl ring (a "syn" position) while the E-isomer is the opposite; i.e., the hydroxyl group is away from the fluorine atom (an "anti" position). The proof of the configuration may be made, e.g. by NMR. Typically, the enriched Z-isomer oxime contains at least 90%, more preferably at least 95% of the Z-isomer and in some embodiments at least 97%, at least 98% or even at least 99% Z-isomer. Because of the discovery that the E-isomer oxime is not merely slower reacting than the Z-isomer oxime but rather is essentially unreactive, the less the amount of the E-isomer oxime content, the more advantageous and productive the synthetic pathway is made.

The enriched Z-isomer oxime can be provided by any suitable technique. That is any technique or method, alone or in combination, that results in an enriched Z-isomer oxime of formula (3) or (7) including the salts thereof, is intended to satisfy the term "providing." Conveniently, an acetic acid salt can be used to provide an enriched Z-isomer oxime. For example, preferentially precipitating an acetic acid salt of the Z-isomer oxime of formula (3) or (7) from a solution containing a mixture of the Z- and E-isomer oximes is one useful technique. The precipitation is "preferential" in that the precipitate, generally crystalline material, contains a higher Z:E ratio than the solution. Thus, the precipitation favors or prefers forming the Z-isomer oxime over the E-isomer oxime. The precipitation can be essentially spontaneous upon formation of the acetic acid salt of the oxime or it can be induced using generally known methods and techniques including, among others, lowering the temperature of the solution, reducing the amount of solvent in the solution, adding a contrasolvent, adding a seeding crystal, or a combination of two or more of these techniques. It is also contemplated that during or after an initial (spontaneous) precipitation, one or more inducement techniques may be applied to enhance the yield. The preferential precipitation can be repeated one or more times as needed by dissolving the precipitate into the same or different solvents to form a new solution and performing another preferential precipitation, until the desired enrichment in Z-isomer oxime is obtained.

Preferably the solution is based on a polar solvent. Generally, the solubility of the acetic acid salt of the E-isomer oxime (3) or (7) is much higher than that of the Z-isomer in water, lower alcohols, and combinations thereof. The lower alcohols have 1 to 6 carbon atoms and preferably are ethanol or n-butanol, although methanol, isopropanol, and n-propanol can also be used. While the solution is based on such solvents, others may also be present in minor amounts. Alternatively, these solvents can be added as contrasolvents in major or minor amounts to induce preferential precipitation.

The acetic acid salts of the oximes of formulae (3) and (7) form a preferred aspect of the present invention. Any salt that results from the acid addition reaction of acetic acid with an oxime of formula (3) or (7) is included within the meaning of an acetic acid salt. The form of the salt is not limited and specifically includes solid state forms such as crystalline forms and liquid or dissolved/dissociated forms. Further, the ratio of acetic acid cation to oxime while normally 1:1 is not limited thereto and includes 2:1 and 1:2 ratios for example. The crystalline forms include any polymorphic forms as well as solvates including hydrates and alcoholates. The ratio of Z:E isomer ranges from 0:1 to 1:0. Preferably the acetic acid salt of an oxime of formula (3) or (7) contains more Z-isomer oxime than E-isomer oxime, more preferably the salt is at least 80% isomerically pure Z-isomer (i.e. enriched Z-isomer), still more preferably at least 90% isomerically pure Z-isomer, etc., as described above for the preferred enriched Z-isomer content.

The acetic acid salt of the oxime of formula (3) or (7) can be formed by contacting an acetic acid with the oxime, usually in a suitable reaction medium, typically a solvent, so as to allow a salt forming reaction to occur. The acetic acid salt can be isolated in solid form if desired. Preferably the reaction occurs in water or a lower alcohol solvent and Z-isomer oxime salt preferentially precipitate as described above. Accordingly, the mother liquor is obtained enriched by the undesired E-isomer oxime. In an advantageous way, even such "waste" may be reprocessed, particularly by isomerization into the Z-isomer, as explained more fully hereinafter.

In another embodiment, the acetic acid salt is formed in conjunction with the formation or synthesis of the oxime of formula (3) or (7). In this embodiment, the formation of the oxime, such as by one of the prior known techniques, is modified so as to include the presence of acetic acid. For example, reacting a ketone of formula (2)

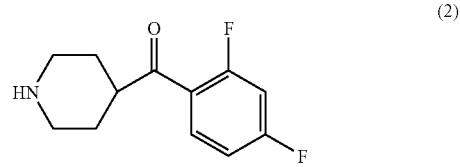

with hydroxylamine in a solvent, preferably n-butanol, in the presence of acetic acid, preferably at least about 1 molar equivalent, can allow for preferential precipitation, and preferably substantially spontaneous preferential precipitation of the formed Z-isomer oxime of formula (3), while the E-isomer remains in the solution. In this way, the synthesis of the oxime of formula (3) can provide an enriched Z-isomer oxime. Similarly, the formation of the oxime of formula (7) can be carried out in the presence of acetic acid to directly produce the acetic acid salt, optionally with preferential precipitation, especially substantially spontaneous preferential precipitation.

The acetate salt of enriched Z-isomer oxime of formula (3) or (7) can be used in further synthesis in the salt form. However, preferably, the oxime is liberated therefrom as a free base, by treatment of the above acetate salt with a suitable base in a suitable solvent. An example of a suitable base is sodium hydroxide, and an example of a suitable solvent is water. Preferably, the liberated Z-isomer oxime base is isolated in solid state such as by filtration or centrifugation.

An enriched Z-isomer oxime of formula (3) or (7) can also be obtained by conversion of the E-isomer oxime into the Z-isomer form. Specifically, by heating the E-isomer, typically a mixture of the Z- and E-isomers, in a solvent, the E-isomer is converted into the Z-isomer. More specifically, the undesired E-isomer of the oxime of formula (3) may be isomerised to the Z-isomer by heating it in an inert solvent, such as, n-butanol, at a sufficient temperature, preferably, higher than 80° C. Furthermore, the heating process may be carried out faster in the presence of an acid catalyst. The acid catalyst may be an acid or an ammonium or amine salt of an acid. The suitable acid catalysts include acetic acid, ammonium acetate, and piperidine acetate. The acid catalyst is preferably present in a molar excess to the oxime, typically at least 2-10:1. For example, when heating essentially pure E-isomer of the oxime of formula (3) with 5 equivalents of acetic acid or ammonium acetate in n-butanol at 110° C., approximately 90% converts into the desired Z-isomer in about 6 hours time. Although both the oximes of formulae (3) and (7) may be used to convert the E-isomer into Z-isomer, the conversion can occur faster with the oxime of formula (3). For example, heating essentially pure E-isomer of the oxime of formula (7) in n-butanol with 5 equivalents of acetic acid at 100° C., a 70% conversion is obtained after 12 hours. Thus, it is preferred to convert the E-isomer into the Z-isomer by heating the oxime of formula (3).

Generally, after cooling the reaction mixture, the produced enriched Z-isomer oxime can be isolated by conventional methods. Preferably, the Z-isomer is converted to an acetic acid salt and preferentially precipitated from the solution and isolated by filtration or centrifugation. When acetic acid is used as an acid catalyst for the conversion, spontaneous crystallization as an acetate salt can occur and/or be induced upon cooling, etc.

In addition, the enriched Z-isomer oxime of formula (3) or (7) can be provided by a combination of preferential precipitation of the acetic acid salt thereof and conversion. For example, the reaction mixture obtained after separation of the Z-isomer oxime acetate (a mother liquor) and which contains the undesired E-isomer oxime acetate can be heated to effect conversion. In particular, such mother liquor can be concentrated or evaporated, mixed with an inert solvent of desirably high boiling point, typically at least 100° C., for instance with n-butanol, and isomerised by heating, e.g. for 2-8 hours, preferably for about 6 hours. After cooling the reaction mixture, the produced (Z)-oxime can be separated by conventional methods, but preferably it spontaneously crystallizes from n-butanol as an acetate salt. For example, the process of making the oxime (3) may be further improved in that the ketone (2) reacts with hydroxylamine in n-butanol under presence of acetic acid, and the reaction mixture is subsequently heated at enhanced temperature to increase the content of the (Z)-oxime by isomerization. The produced (Z)-oxime (3) precipitates from the reaction mixture as the acetate salt.

In summary, essentially all the oxime (3), whenever produced by an oximation reaction, may be obtained as a substantially pure Z-isomer, if using the above procedures according to the invention. Additionally, the enriched Z-isomer oxime of formula (7) can be obtained not only by preferential precipitation of an acetate salt and/or by conversion/isomerization, but it can also be provided synthetically by using an enriched Z-isomer oxime of formula (3) as the starting material. Suitable reaction conditions for converting the oxime of formula (3) into the oxime of formula (7) are described in the above-mentioned prior art.

Having provided an enriched Z-isomer oxime of formula (3) or (7) or salt thereof, the oxime is converted to risperidone, with or without isolation of the enriched Z-isomer oxime and if in a salt form, with or without converting to the oxime free base form. "Converting" to risperidone means any one or more reaction steps that result in the transformation of the oxime of formula (3) or (7) into risperidone or a salt thereof. The "converting" process can include cyclization and/or alkylation of the enriched Z-isomer oxime to form the end product of risperidone. In this context, cyclization refers to the ring forming reaction wherein the oxime moiety together with other atoms is converted into a benzisoxazole moiety and alkylation refers to alkylating the ring nitrogen of the piperidinyl moiety. However, any process may be used to convert the enriched Z-isomer oxime to form the end product risperidone. The following chart illustrates several convenient pathways for making risperidone.

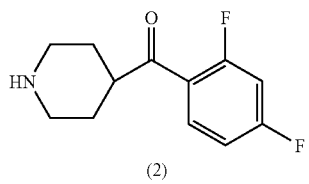

(2)

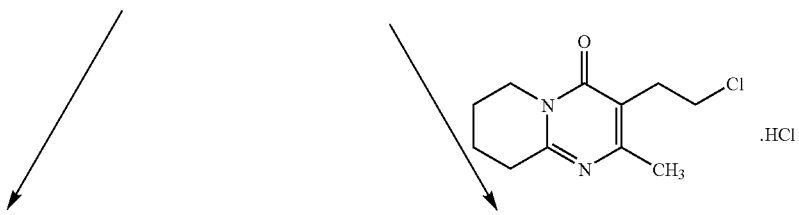

-continued
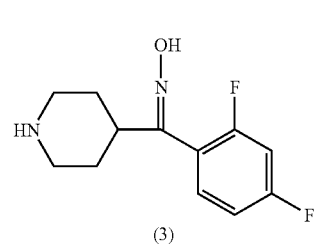
(3)
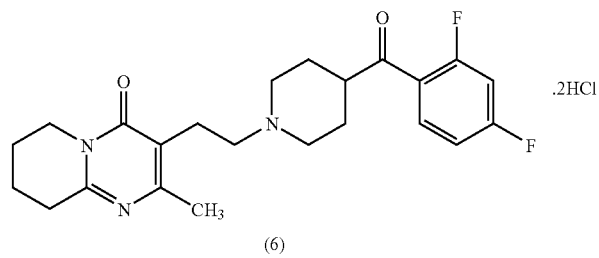
(6)
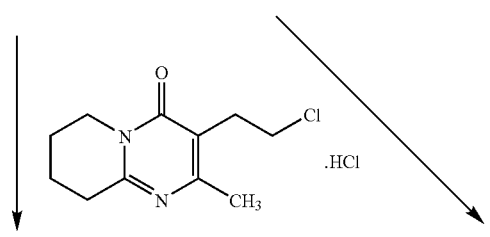
.HCl
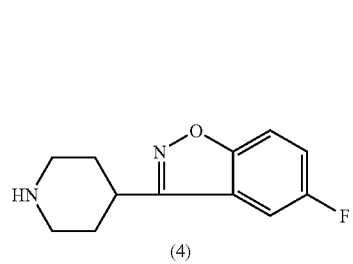
(4)
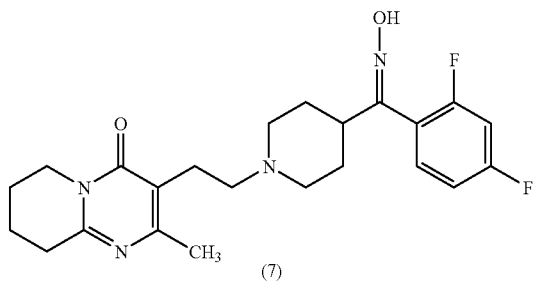
(7)
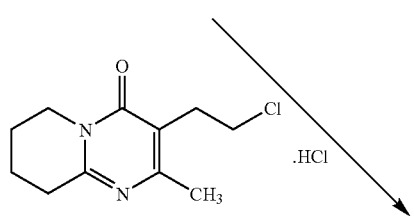
.HCl
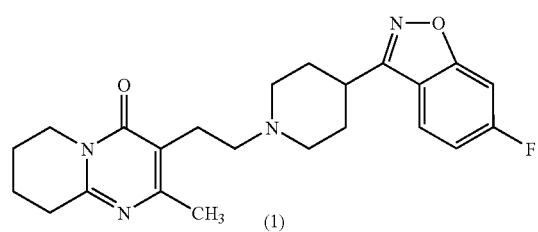
(1)

Conveniently, the enriched Z-isomer oxime of formula (3) may be converted to risperidone by a process that comprises cyclizing and alkylating. For example, first converting the enriched Z-isomer oxime to the benzisoxazole compound (4) by a cyclization reaction using a base, followed by alkylation of compound (4) with the chloroethyl compound (5) to form risperidone.

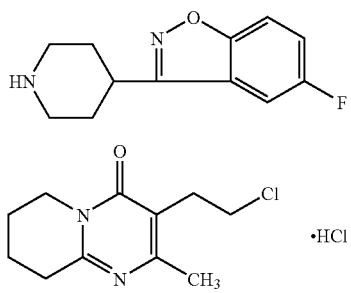

Additionally, the enriched Z-isomer oxime can be converted to risperidone by the Z-isomer oxime first alkylating with the chloroethyl compound (5) to yield an alkylated oxime (7). The alkylated oxime (7) is then cyclized to risperidone under treatment with a base. Accordingly, the oxime (3) is alkylated with the chloroethyl compound (5) in acetonitrile under presence of a suitable base, preferably potassium carbonate. The alkylation of the oxime (3) with compound (5) proceeds readily by heating under reflux for several hours, preferably between 3-5 hours. Upon dilution with water, or any dilutent, and optional adjustment of pH, the alkylated oxime (7) precipitates from the reaction mixture at room temperature. It may be isolated and dried by conventional techniques. The relative content of the Z-isomer in the produced oxime (7) (Z/E isomer ratio) after alkylation with (5) is approximately the same as in the starting oxime (3). Thus no racemization occurs during the alkylation reaction with the chloroethyl compound (5) under conventional conditions. As no racemization proceeds, the alkylation may provide the Z-isomer of the oxime (7) substantially free from the E-isomer, if starting from the accordingly pure Z-isomer of the oxime (3). For instance, the obtained alkylated oxime (7) is enriched preferably by more than 95% of the desired (Z) isomer.

The enriched Z-isomer oxime of formula (7) can be converted to risperidone by cyclization. For example, conversion may occur by a process of a cyclization under presence of a base, with the specific feature that the yield of the obtained risperidone is higher and the content of the contaminating side products, particularly the uncyclized E-oxime (7), is lower. Suitable solvent for cyclization can be water, lower alcohol, such as methanol, ethanol or isopropanol, suitable base is an alkali metal hydroxide, such as, sodium hydroxide.

The above techniques for converting the enriched Z-isomer oxime into risperidone are not exhaustive; other techniques can also be used. Further, all of the above reagents and reaction partners are readily available and/or can be made from known or commercially available starting materials using known methods and techniques.

The risperidone is preferentially isolated from the reaction mixture as a free base, which is a solid, and the crude product may be optionally further purified, e.g. by a recrystallization from a suitable solvent. Examples of such solvents are given, e.g., in WO 02/14286.

The publicly available, under FOIA, Summary Basis of Approval of US New Drug Application 20-272, incorporated herein by reference, teaches that risperidone base may be isolated in two polymorphic modifications, one of them being thermodynamically stable. Such modification (Form A) exhibits a melting point of about 169-173° C. and was obtained by crystallization from ethanol. Also the crystalline structure of risperidone base was determined by single crystal X-ray diffraction by Peeters et al in Acta Cryst. (1993), C49, 1698-1700. From these data, X-ray powder diffraction pattern (XRPD) may be simulated. The risperidone product obtained by crystallization from ethanol (the Form A) has crystalline structure corresponding to that shown in the cited article. In the present invention, the same solid state product (form A) and having the same properties may also be obtained by crystallization from most ordinary solvents, such as an alcohol/water mixture or isopropanol.

In a preferred mode of crystallization, a water/ alcohol solvent mixture is used. More preferably, the crude risperidone base is dissolved in water by aid of an acid, e.g. acetic acid, alcohol is added and the acid is neutralized by a base, e.g. sodium hydroxide. This technique allows the use of higher concentrations of risperidone and lower, even ambient, crystallization temperatures, thus improving economy of the process and purity of the product. The produced risperidone is typically a white or off-white crystalline product. Its purity, as determined by HPLC, is typically higher than 99% and it contains less than 1% of related impurities, particularly is essentially free (less than 0.2%, and preferably below limits of detection) from 9-hydroxy risperidone. Dried risperidone product is also essentially free from bound water or other solvents. Typically, it contains less than 5%, preferably less than 1% of water or a solvent, particularly alcohol. For pharmaceutical applications, a product with an average particle size of less than 100 microns is preferred.

The invention is further illustrated by the following non-limiting examples:

EXAMPLES

Example 1

Preparation of Z- and E-isomers of the oxime (3)

Step 1

19.9 g of hydroxylamine hydrochloride is suspended in 200 ml of ethanol and 38.2 g of 50% water solution of sodium hydroxide is added. The suspension is stirred for 10 min. 50 g of 4-(2,4-difluorobenzoyl) piperidine hydrochloride is added and the suspension stirred for the next 10 min. Then the crystals are filtered off and washed with 2×25 ml of ethanol. 25 g of ammonium acetate is added to the filtrate and the reaction mixture agitated at 60° C. for 10 hrs. The reaction mixture is acidified with 6.5 ml of acetic acid and cooled to −15° C. for 4 hours. A white solid is filtered off and washed at −15° C. with 2×25 ml of ethanol. The product is air-dried. Yield: 43.42 g (75.7% of theoretical yield) of Z-isomer oxime (3) acetate.

Step 2

The solvent is evaporated from the mother liquor of the Step 1 at 70° C. and the oily residue diluted with 100 ml of water and acidified with 10 ml of acetic acid. The solution is extracted with 3×50 ml of ethyl acetate, the ethyl acetate extracts are extracted with 50 ml of water. 100 ml of ethyl acetate is added to the water solution and the emulsion alkalinized to pH=11 with 50% NaOH. The water layer is extracted with next 3×50 ml of ethyl acetate. Collected ethyl acetate solutions are extracted with 50 ml of water. The solvent is evaporated at 70° C. The crude product is dissolved in 410 ml of ethyl acetate at 77° C. A clear solution is slowly cooled and a suspension obtained. The crystallization was finished by standing in a refrigerator at −15° C. for 14 hours. The crystals are filtered off and washed with 2×20 ml of ethyl acetate. The crystals are air-dried. Yield: 13.15 g (28.5% of theoretical yield) of E-isomer oxime (3).

Step 3

43.42 g of risperidone oxime Z-isomer acetate from Step (1) is suspended in 170 ml of water and the suspension alkalized with 50% NaOH to pH=10 and stirred for 1 hour at room temperature. The white solid is filtered off and washed with 3×100 ml of water. The product is air-dried. Yield: 27.79 g (60.5% of theoretical yield) of Z-isomer oxime (3).

Example 2

Z-Isomer of the Oxime Compound (3)

Step 1—Acetate Salt of the Z-Isomer of the Oxime (3)

15.93 g of hydroxylamine hydrochloride is suspended in 125 ml of ethanol and 33.62 g of 50% water solution of sodium hydroxide is added dropwise at 20-30° C. After 15 minutes of stirring, 32.8 ml of acetic acid and 50 g of 4-(2,4-difluorobenzoyl)piperidine hydrochloride is added. The suspension is then heated for 7 hours at 78-80° C. (reflux). The solid is then filtered off after 1 hour of agitating at 20° C. and is then washed with 2×30 ml of ethanol. Yield: Wet product containing 63.43 g of dry substance comprising Z-oxime (3) acetate. Purity (HPLC): 98.3%.

Step 2—Isomerization of the (E)-Oxime(3) Acetate to the (Z)-Oxime (3)Acetate

The filtrate from the step (1) is evaporated to approx. 35 ml at reduced pressure and 15 ml of n-butylalcohol is added. The suspension is heated for 6.5 hours at 110° C. The reaction mixture was cooled to 20° C. and agitated for 1 hour. White solid is filtered off and washed with 10 ml of ethanol. Yield: Wet product-containing 17.3 g of Z-oxime (3) acetate. Purity (HPLC): 97.0%

Step 3—Recovery of the Z-Oxime (3) from the Z-Oxime(3) Acetate

Both parts of wet Z-oxime(3) acetate from step 1 and step 2 are suspended in 230 ml of water at 60° C. and the suspension is alkalinized with 68 ml of 10% NaOH to pH=10. The suspension is agitated for 30 minutes at 60° C. and 60 minutes at 20° C. The solid is filtered off and washed with 2×10 ml of water. The crystals are dried. Yield: 44.5 g (96.9%) of Z-oxime (3) base. Purity (HPLC): 98.6%

Example 3

Preparation of Z-Isomer of the Oxime (7)

1.11 g of potassium iodide, 51.2 ml of acetonitrile, 8.76 g of 3-(2-chloroethyl)-2-methyl-6,7,8,9-tetrahydro-4H-pyrido[1,2a]pyrimidin-4-one hydrochloride, 4.6 g of potassium carbonate and 8.0 g of Z-oxime (3) base are mixed. The suspension is heated at reflux (78° C.) for 3.5 h. The reaction mixture is cooled to room temperature and 104 ml of water is added. The pH of the suspension is adjusted to 10 (50% KOH) and is agitated at room temperature for 4 hrs. The crystals are filtered off, washed with 30 ml of water and dried. Yield: 13.42 g (93.6% of theoretical yield). Purity (HPLC): 96.23%

Example 4

(Z)-Oxime (7) from (Z)-Oxime (3) Acetate 22.9 g of the 3-(2-chloroethyl)-2-methyl-6,7,8,9-tetrahydro-4H-pyrido[1,2a]pyrimidin-4-one hydrochloride, 26.1 g of Z-oxime (3) acetate and 4.6 g of potassium iodide were suspended in 92 ml of ethanol and 20.5 g of 50% KOH was added. The suspension was stirred at 70° C. for 11 hours. The reaction mixture (pH=9) was evaporated to dryness, the residue was dissolved in 350 ml of water and was extracted with 3×350 ml of ethyl acetate. Collected organic layers were extracted with 2×500 ml of 2% acetic acid and the organic layer was extracted with 50 ml of water. The water extracts were alkalized with 35 ml of 50% KOH to pH=10-10.5. The emulsion was extracted with 2×400 ml of ethyl acetate and then with 2×200 ml of ethyl acetate. Ethyl acetate layers were extracted with 100 ml of water and 50 ml of saturated brine. The organic solution was evaporated at 70° C. Yield: 26.0 g (69.4% of theoretical yield) of crude oxime (7) base Z-isomer. The residue was dissolved at 80° C. in 250 ml of ethanol. The solution was slowly cooled to 20° C. and stirred for 1 hour; then cooled to −15° C. and let stand for 12 hours. The crystals were filtered off and washed with 2×10 ml of ethanol.

Yield: 17.86 g (47.7% of theoretical yield) of crystallized oxime (7) base Z-isomer (purity 97.6%).

Example 5

Preparation of the (E)-Oxime (7)

13.0 g of 4-(2,4-difluorobenzoyl)piperidine hydrochloride, 14.83 g of E-oxime (3) acetate and 2.6 g of potassium iodide are suspended in 52 ml of ethanol and 11.6 of 50% KOH is added. The suspension is stirred at 60° C. for 9 hours. The reaction mixture (pH=9) was evaporated to dryness, the residue was dissolved in 200 ml of water, pH was set up to 10-10.5 and the product was extracted with 3×200 ml of chloroform. Collected organic layers are extracted with 50 ml of water, 500 ml of 2% acetic acid and then 2×250 ml of 2% acetic acid. The water extract is alkalized with 50% NaOH to pH=10.5 and the solution extracted with 3×150 ml of chloroform. Chloroform solution is extracted with 2×50 ml of water. The solvent is evaporated at 60° C. Yield: 25.35 g of crude E-isomer oxime (7) base. The residue is dissolved at 80° C. in 122 ml of methanol. The solution is slowly cooled to 20° C. and stirred for 1 h. Then it is cooled to −15° C. and left standing for 12 hours. The crystals are filtered off and washed with 2×10 ml of methanol. Yield: 10.34 g (48.6% of theoretical yield) of crystallized oxime (7) base E-isomer.

Example 6

Cyclization Experiments on the Oxime (7)

0.2 g of essentially pure Z- or E-isomer of the oxime (7) is attempted to be converted into risperidone by dissolving in 2 ml of ethanol, adding 0.1 g of 50% aqueous KOH and heating the mixture under stirring at 80° C. Samples of the reaction mixture are taken and analyzed by HPLC.

|  | Results of HPLC (in area %): | | | |
|---|---|---|---|---|
|  | t = 0 | t = 1 | t = 3 | t = 5 hrs |
| a) | | | | |
| E-oxime (7) | 99.6 | 91.5 | 91.5 | 90.0 |
| Risperidone: | 0 | 3.7 | 4.0 | 4.2 |

-continued

| | Results of HPLC (in area %): | | | |
|---|---|---|---|---|
| | t = 0 | t = 1 | t = 3 | t = 5 hrs |
| b) | | | | |
| Z-oxime(7) | 97.6 | 0.7 | 0.6 | 0.5 |
| Risperidone | 0 | 97.8 | 96.7 | 95.5 |

Observations

Sub a): Adding another KOH and prolonged heating did not lead to an increase of risperidone in the reaction mixture.

Sub b): One hour is sufficient to perform a conversion. Prolonged heating leads to an increased amount of by-products.

Example 7

Cyclization Experiments on Oxime (3)

0.2 g of essentially pure Z- or E-isomer of the oxime (3) is attempted to convert into the benzisoxazole compound (4) by dissolving in 2 ml of ethanol, adding 0.18 g of 50% aqueous KOH and heating the mixture under stirring at 80° C. Samples of the reaction mixture were taken and analyzed by HPLC.

| | Results of HPLC (in area %): | | | |
|---|---|---|---|---|
| a) | t = 0 | t = 2 | t = 4 | t = 6 hrs |
| E-oxime (3) | 99.3 | 88.4 | 88.5 | 89.2 |
| Benzisoxazole (4): | 0 | 7.1 | 7.1 | 7.4 |
| b) | t = 0 | t = 1 | t = 2 hrs | |
| Z-oxime(3) | 97.7 | 1.0 | 1.0 | |
| Benzisoxazole (4): | 0 | 96.9 | 96.5 | |

Example 8

Risperidone from the Z-oxime (7)

85 ml of ethanol, 6.97 g of sodium hydroxide, 3.32 g of borax and 50.0 g of the Z-oxime (7) are agitated for 30 min. at 70° C. The reaction mixture is diluted with 200 ml of water at 40° C. and the suspension is agitated for 2 hours at room temperature. The crystals are filtered off, washed with 25 ml of water and dried. Yield: 45.26 g (94.9% of the theoretical yield) of crude risperidone. Purity (HPLC): 97.2%

Example 9

Risperidone from Z-Oxime (7)

1.7 ml of ethanol, 0.40 g of 50% solution of potassium hydroxide, 0.07 g of borax and 1.00 g of oxime (7) Z-isomer base are agitated at 40° C. for 15 min. The temperature is increased to 70° C. and the suspension agitated for 15 minutes. The reaction mixture is diluted with 8.0 ml of water and the suspension agitated for 1 hour at room temperature. The crystals are filtered off, washed with 10 ml of water and dried. Yield: 0.8 g (83.9% of theoretical yield) of risperidone.

Example 10

Crystallization of Risperidone from 2-Propanol/Water 5.08 g of risperidone is dissolved at room temperature in 10.2 ml of water and 0.81 g of acetic acid. The solution is filtered and diluted with 20.3 ml of water and 10.2 ml of isopropanol. To the stirred solution is added dropwise a solution of 1.52 g of 50% sodium hydroxide solution in 10.2 ml of water. Upon completion, stirring was continued for 1 hour at 70° C. The crystals are filtered off and washed with 2.0 ml of water. The product is dried in air. Yield: 4.73 g (93.11% of theory). DSC: Form A.

Example 11

Crystallization of Risperidone from Ethanol/Water 5.05 g of risperidone is dissolved at room temperature in 10.1 ml of water and 0.81 g of acetic acid. The solution is filtered and diluted with 20.2 ml of water. The solution is poured dropwise into a solution of 1.52 g of 50% sodium hydroxide solution in 10.1 ml of water and 10.1 ml of ethanol. Upon completion, stirring is continued for 1 hour at 25° C. temperature. The crystals are filtered off and washed with 2.0 ml of water. The product is dried in air. Yield: 4.68 g (92.67% of theory). DSC: Form A.

Example 12

Crystallization of Risperidone from N,N-dimethylformamide 5.62 g of risperidone is dissolved at 78° C. in 62.0 ml of N,N-dimethylformamide. The solution is cooled to 20° C. The mixture is stirred for 1 hour. The crystals are filtered off and washed with 2×3 ml of 2-propanol. The product is dried. Yield: 3.95 g (70.29% of theory). DSC: Form A.

Example 13

Crystallization of Risperidone from 2-propanol 5.62 g of risperidone is dissolved at 78° C. in 82.0 ml of 2-propanol. The solution is cooled to 20° C. The mixture is stirred for 1 hour. The crystals are filtered off and washed with 2×3 ml of 2-propanol. The product is dried. Yield: 4.60 g (81.85% of theory). DSC: Form A.

Example 14

Crystallization of Risperidone from Ethanol/Water 5.00 g of crude risperidone is suspended in 10 ml of water and 0.80 g of acetic acid is added. After dissolving, the solution is filtered. The clear solution diluted with 30 ml of ethanol and then alkalized dropwise during 20 minutes with a solution of 1.5 g of 50% sodium hydroxide in 10 ml of water at 35-40° C. (pH=9.5-10). The suspension is agitated at 20° C. for 1 hour. The product is filtered off and washed with 5 ml of distilled water (neutral reaction). Yield: 3.91 g (78% of the theoretical yield)

Example 15

Crystallization of Risperidone from Methanol/Water 5.00 g of crude risperidone is suspended in 10 ml of water and 0.80 g of acetic acid is added. After dissolving, the solution is filtered. The clear solution is diluted with 30 ml of methanol. The solution is alkalized dropwise during 20 minutes with a solution of 1.5 g of 50% sodium hydroxide in 10 ml of water at 35-40° C. (pH=9.5-10). The suspension is agitated at 22° C. for 1 hour. The product is filtered off and was washed with 5 ml of distilled water (neutral reaction). Yield: 4.61 g (92% of the theoretical yield).

Example 16

Crystallization of Risperidone from Ethanol 5 g of risperidone is dissolved in 20 ml of ethanol at reflux. The solution is cooled spontaneously to ambient temperature and agitated for 1 hour. The crystals are filtered off and dried. Yield: 4.58 g (91.6% of the theoretical yield). DSC: Form A.

Example 17

Crystallization of Risperidone from Methanol 6 g of risperidone is dissolved in 21.8 ml of methanol at reflux. The solution is cooled spontaneously to ambient temperature and agitated for 1 hour. The crystals are filtered off and dried. Yield: 4.77 g (80% of the theoretical yield). DSC: Form A.

Each of the patents, articles, and publications mentioned above is incorporated herein by reference in its entirety. The invention having been thus described, it will be obvious to the worker skilled in the art that the same may be varied in many ways without departing from the spirit of the invention and all such modifications are included within the scope of the present invention as set forth in the following claims.

What is claimed is:

1. An acetic acid salt of a compound of formula (3) or (7):

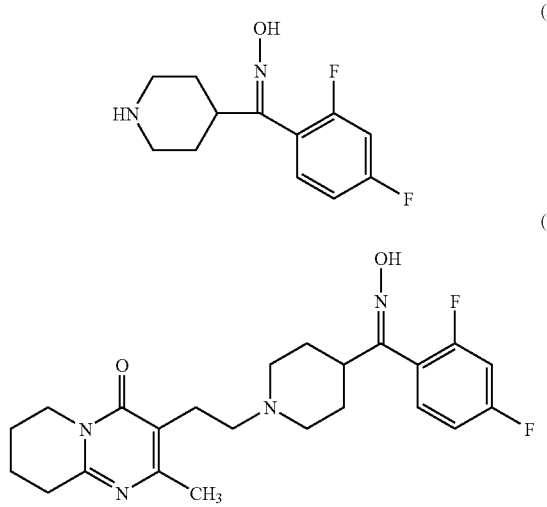

wherein said salt of formula (3) contains more of the Z-isomer of formula (3) than of the E-isomer of formula (3).

2. The acetic acid salt according to claim 1, wherein said salt is in solid form.

3. The acetic acid salt according to claim 1, wherein said salt is the salt of said compound of formula (3).

4. The acetic acid salt according to claim 3, wherein said salt is in solid form and is at least 90% isomerically pure Z-isomer of formula (3).

5. The acetic acid salt according to claim 1, wherein said salt is the salt of said compound of formula (7).

6. The acetic acid salt according to claim 5, wherein said salt contains more of the Z-isomer of formula (7) than of the E-isomer of formula (7).

7. The acetic acid salt according to claim 6, wherein said salt is in solid form and is at least 90% isomerically pure of Z-isomer of formula (7).

8. An enriched Z-isomer oxime of formula (3) or (7):

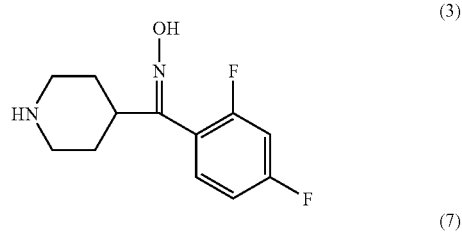

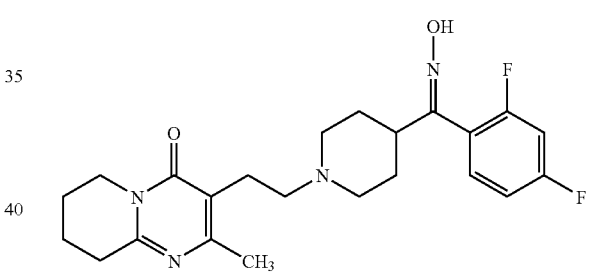

wherein the amount of Z-isomer is at least 95%, based on the total amount of said oxime.

9. The enriched Z-isomer according to claim 8, wherein said oxime is a compound of formula (3).

10. The enriched Z-isomer according to claim 8, wherein said oxime is a compound of formula (7).

* * * * *